United States Patent [19]

Takishima et al.

[11] Patent Number: 5,178,156

[45] Date of Patent: Jan. 12, 1993

[54] APNEA PREVENTIVE STIMULATING DEVICE

[75] Inventors: Tamotsu Takishima; Wataru Hida; Hiroshi Miki, all of Sendai, Japan

[73] Assignee: Chest Corporation, Tokyo, Japan

[21] Appl. No.: 537,028

[22] Filed: Jun. 12, 1990

[30] Foreign Application Priority Data

Jun. 20, 1989 [JP] Japan .................................. 1-157218

[51] Int. Cl.⁵ ........................ A61B 5/087; A61N 1/32
[52] U.S. Cl. ..................................... 128/724; 128/421
[58] Field of Search ............... 128/716, 724, 725, 421; 340/573, 575

[56] References Cited

U.S. PATENT DOCUMENTS

| | | | |
|---|---|---|---|
| 3,802,417 | 4/1974 | Lang | 128/724 X |
| 4,420,001 | 12/1983 | Hearne | 128/724 |
| 4,715,367 | 12/1987 | Crossley | 128/724 X |
| 4,777,963 | 10/1988 | McKenna | 128/724 |
| 4,830,008 | 5/1989 | Meer | 128/421 |

FOREIGN PATENT DOCUMENTS 2575911 7/1986 France .................................. 128/724

OTHER PUBLICATIONS

Chess et al, "Apnoea monitor . . ." Med. & Biol. Eng., vol. 14, No. 1, pp. 97-100, Jan. 1976.

Primary Examiner—Lee S. Cohen
Attorney, Agent, or Firm—Emmanuel J. Lobato; Robert E. Burns

[57] ABSTRACT

The sleep-apnea syndrome is classified into a so-called central type caused by an abnormality in the respiratory center, an obstructive type by an upper airway obstruction, and a mixed type by a combination thereof. Among the rest, the obstructive type is often observed clinically and is considered to be caused by a morphological abnormality in the upper airway tract, such as tonsillar hypertrophy or micrognathia, or by a tonus of the upper airway muscle for broadening the airway. The inventors of this application have clarified by experiments that the upper airway can be recovered from obstruction which causes apnea stimulating the genioglossus, which is one of the dilator muscles of the upper airway, with pulses of a frequency of 40 to 150 Hz, a peak value of 1 to 50 volts and a rise-up time constant of 0.2 seconds or more, and that control of the start and stop of the electric stimulation with apnea detection signals would make it possible to automatically take measures to deal with apnea even at night when it is particularly difficult to find a fit of apnea.

4 Claims, 5 Drawing Sheets

Fig. 3D

|←— 5 sec —→|
t₁    t₂    t₃

BREATHING STATE-I | NON-BREATHING STATE-II | BREATHING STATE-I

APNEA PREVENTIVE STIMULATING DEVICE

BACKGROUND OF THE INVENTION

The present invention relates to an apnea preventive stimulating device for preventing the occurrence of trouble which results from abnormality in the respiratory function in one's sleep.

Many studies have been reported on a so-called sleep-apnea syndrome, i.e. apnea which is accompanied by the suspension of breathing, for example, for 10 seconds or more in one's sleep at night. Such apnea in one's sleep decreases the alveolar ventilation volume and the partial pressure of arterial oxygen difference ($PaO_2$) and increases the partial pressure of arterial carbon dioxide ($PaCO_2$), and further, it lowers the chemoreceptor sensitivity and raises the upper airway resistance, thus constituting a causative factor in aggravation of the arterial blood gas. This causes pulmonary hypertension, right-sided heart failure, arrhythmia, or brain trouble, which may sometimes result in a sudden death if worst comes to worst. Thus, the breathing abnormality in one's sleep is a clinically important subject, and it is necessary to take measures for preventing the occurrence of the above-mentioned sleep-apnea.

SUMMARY OF THE INVENTION

An object of the present invention is to provide a device effective for preventing the above-mentioned sleep-apnea.

To attain the above object of the present invention, there is provided an apnea preventive stimulating device characterized by the provision of: a respiration sensing circuit; a detection signal generator for detecting a respiration detection signal from the output of said respiration sensing circuit; an electric stimulating wave generating circuit which, when apnea has continued for 5 to 10 seconds after its detection by said detection signal generator, starts to operate and generates electric stimulating waves having a frequency of 40 to 100 Hz and a pulse peak value of 1 to 50 V; and a stimulating circuit composed of genioglossus stimulators which are supplied with the output of the said electric stimulating wave generating circuit.

The respiration sensing circuit is formed by a parallel circuit of sensors for sensing respiration through both nostrils and a sensor for sensing respiration through a mouth, or a microphone sensor to detect the breath tones. The intensity of the electric stimulating waves can be amplified at a predetermined time from a patient's bedtime, so that the lowering of stimulation on a patient by the electric stimulating wave during the patient's deep sleep is compensated for to wake up the patient.

The sleep-apnea syndrome is classified into a so-called central type caused by an abnormality in the respiratory center, an obstructive type by an upper airway obstruction, and a mixed type by a combination thereof. Among the rest, the obstructive type is often observed clinically and is considered to be caused by a morphological abnormality in the upper airway tract, such as tonsillar hypertrophy or micrognathia, or by a tonus of the upper airway muscle for broadening the airway.

The inventors of this application have clarified by experiments that the upper airway can be recovered from obstruction which causes apnea stimulating the genioglossus, which is one of the dilator muscles of the upper airway, with pulses of a frequency of 40 to 150 Hz, a peak value of 1 to 50 volts and rise time constant of 0.2 seconds or more, and that control of the start and stop of the electric stimulation with apnea detection signals would make it possible to automatically take measures to deal with apnea even at night when it is particularly difficult to find a fit of apnea.

BRIEF DESCRIPTION OF THE DRAWINGS

The present invention will be described in detail below with reference to the accompanying drawings, in which:

FIGS. 2, 5 and 8 are schematic diagrams each showing the positions where to fix respiration detecting sensors and so on;

DETAILED DESCRIPTION

Figure 1:
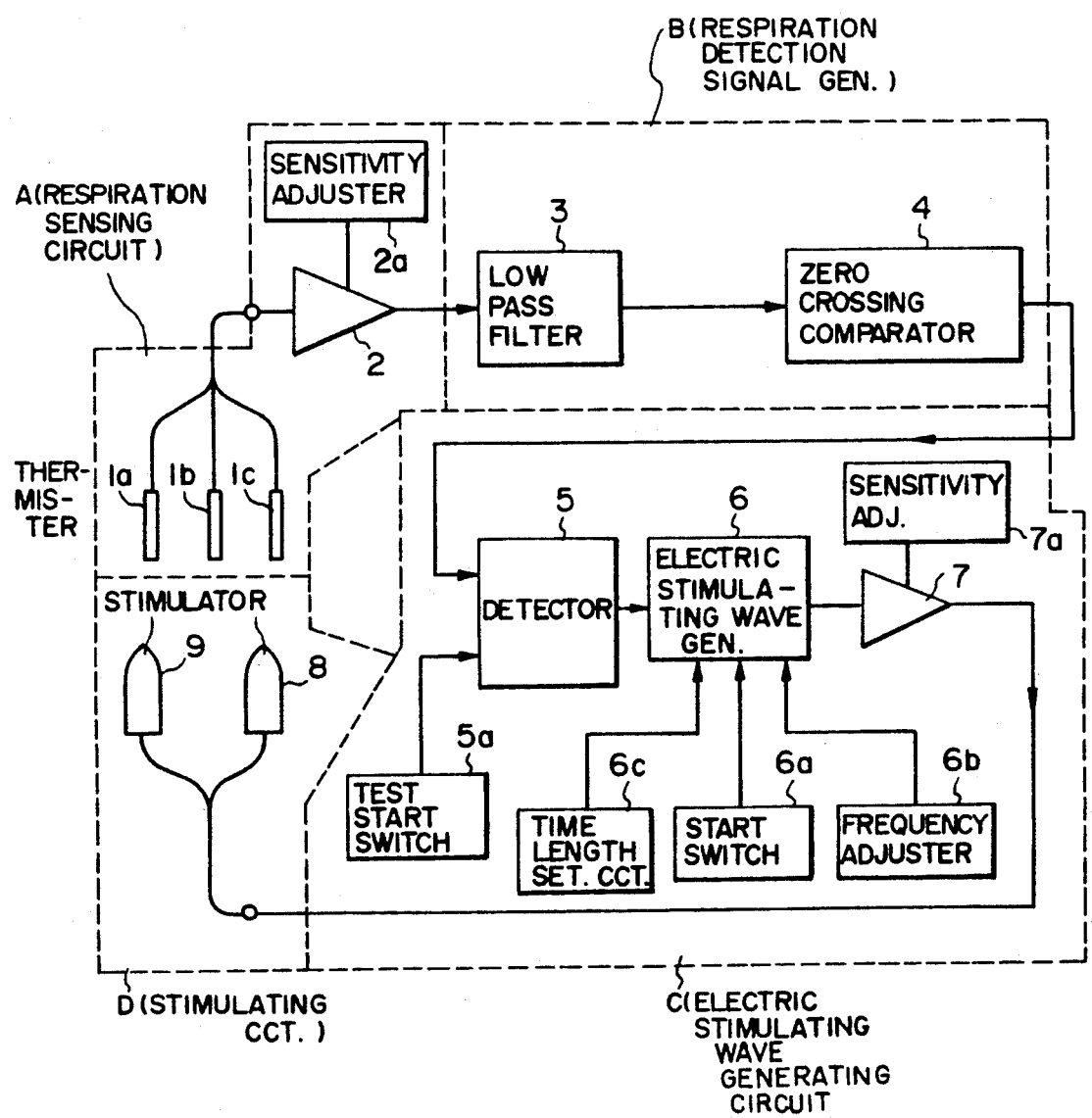
FIG. 1 is a circuit diagram illustrating an embodiment of the present invention.

With reference to FIG. 1 illustrating an embodiment of the present invention, reference character A indicates a respiration sensing circuit, which includes the following elements. Reference numerals $1a$, $1b$ and $1c$ designate thermistors. The thermistors $1a$ and $1b$ are provided in anticipation of stuffing up of one of a patient's nostrils, for detecting one's respiration airflow through the both nostrils, and the thermistor $1c$ is provided in anticipation of stuffing up of both nostrils, for observing respiration through the mouth. These thermistors detect temperature variations caused by warm and cold air currents resulting from expiration and inspiration which are alternately repeated.

Figure 3A:
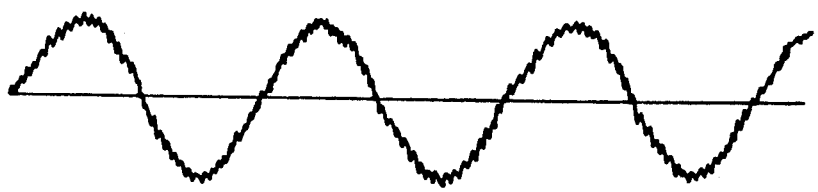
FIGS. 3A–3C show waveform diagrams explanatory of the operation of this invention device.
Figure 2:
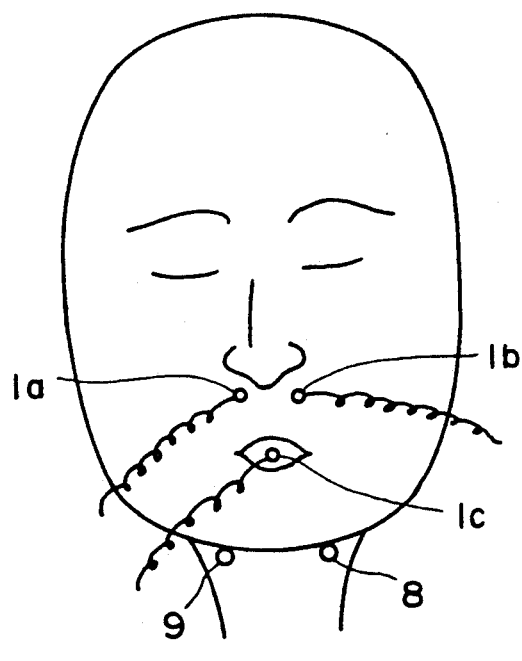

As shown in FIG. 2, the thermistors are fixed as by a tape on the skin at the nostrils and on the mouth. The outputs of the thermistors $1a$, $1b$ and $1c$ are connected in parallel to ensure checking whether the patient is breathing or not, even if two of the thermistors $1a$, $1b$ and $1c$ cannot detect the respiration because of their dislocation or patient's nosal congestion. The respiration sensing circuit A formed by the thermistors yields such a substantially sinusoidally varying output signal as shown in FIG. 3A which goes positive and negative in response to the warm and cold air currents when the patient expires and inspires, respectively. Reference numeral 2 identifies a sensor amplifier. By adjusting its amplification factor the detection sensitivity can freely be set so that a detection signal of a sufficiently high level can be obtained although the amount of respiration differs with individual patients.

Figure 3B:
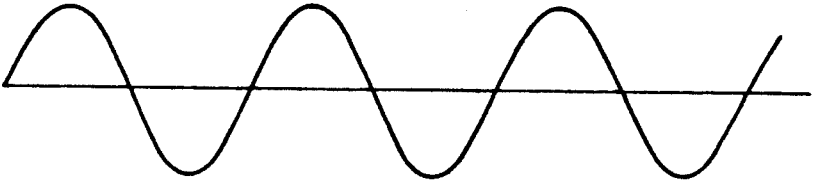
Figure 3C:
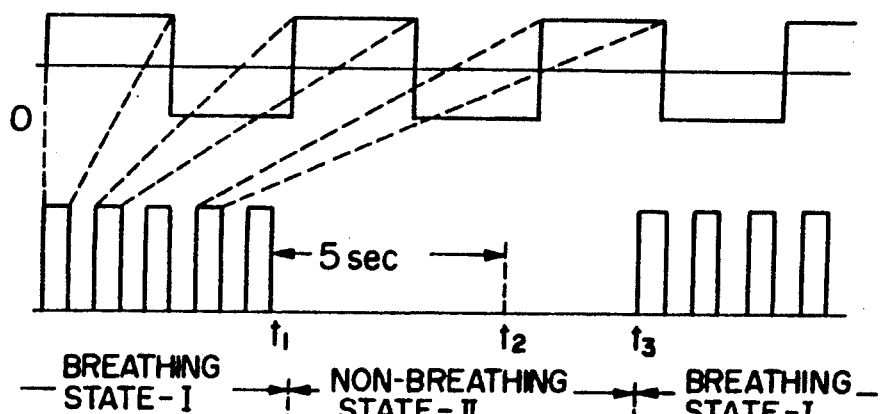

Reference character B denotes a respiration detection signal generator, which includes the following elements. Reference numeral 3 indicates a low-pass filter, which filters out noise signals from the low-frequency respiration detection signal available from the respiration sensing circuit A as shown in FIG. 3B. Reference numeral 4 denotes a zero crossing comparator, which provides a train of pulses which rise and fall at the zero points when the output waveform of FIG. 3B rises and falls, respectively, as shown in FIG. 3(c). The pulses are level shifted as depicted in FIG. 3D, thus producing a respiration identification signal which is not delivered during the patient's non-breathing state II.

Figure 3E:

Reference character C indicates an electric stimulating wave generating circuit, which includes the following elements. Reference numeral 5 denotes a respiration identifying detector, which is formed by a retriggerable one-shot multivibrator circuit, for example, and its operation time constant is set to a value of 5 to 10 seconds which does not introduce the possibility of trouble being caused by apnea. This circuit operates in such a manner that its output is held high-level as shown in FIG. 3E by the successive application thereto of the pulses of FIG. 3D during the patient's breathing state I and when the breathing state is altered to the non-breathing state II at a time $t_1$ and the respiration identification signal is no longer applied, the output still remains high until a time $t_2$ after a certain elapsed time, for example, 5 seconds, thereafter going low. Reference numeral 5a denotes a start switch for test use.

Reference numeral 6 indicates an electric stimulating wave generator, which is provided with a switch 6a for manually starting its operation so that electric stimulating waves can be generated at any time for checking out the oscillation of the stimulating wave generator. A frequency setting knob 6b is provided so that the repetition frequency of stimulation suitable to each patient can be adjusted in the range of between 40 and 150 Hz. Further, a time length setting circuit 6c is provided, by which the generation of stimulating waves is automatically stopped when the state of apnea continues over a certain period of time and recovery from apnea can no longer be expected.

Figure 3F:
Figure 3G:
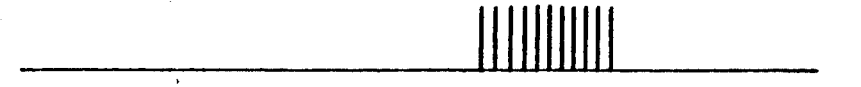

In a case where the patient lapses into the non-breathing state II at the time $t_1$ as shown in FIG. 3D and the output of the one-shot multivibrator circuit 5 goes low at the time $t_2$ five seconds thereafter as depicted in FIG. 3E, the electric stimulating wave generator starts to operate as shown in FIG. 3F and delivers electric stimulating waves as shown in FIG. 3G. When the respiration is recovered by the stimulation at a time $t_3$ and the output of the one-shot multivibrator circuit 5 goes high again as depicted in FIG. 3F, the electric stimulating wave generator stops its operation and hence stops the generation of the electric simulating waves as shown in FIG. 3G. Reference numeral 7 indicates a stimulating wave amplifier and 7a denotes a stimulation sensitivity adjuster, by which the amplification factor of the amplifier can be adjusted for setting its output voltage level within the range of 1 to 50 volts as desired.

Figure 5:
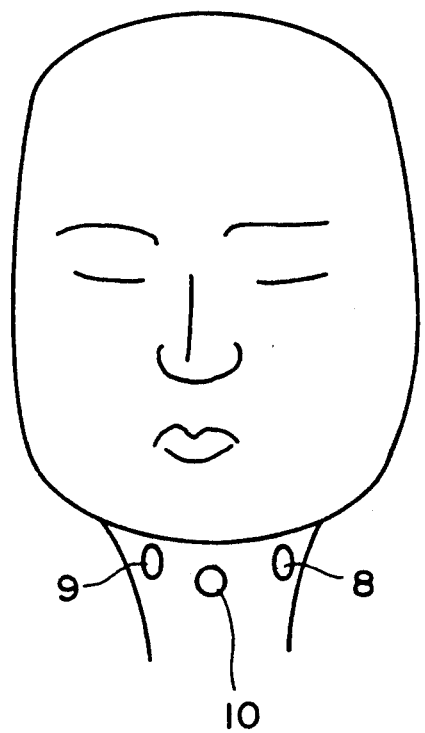

Reference character D identifies a stimulating circuit composed of two conductive stimulating elements 8 and 9, which are fixed as by tape to the skin surface at the lower jaw at both sides of the Adam's apple as shown in FIG. 5. The electric stimulating waves are applied to the genioglussus by the output of the electric stimulative wave generator 6 which is supplied to the stimulators 8 and 9.

The thermister sensor for detecting the air flows from the mouth and the nose is subjected to set the sensor and any necessary cord on the person's face. This disturbs a person in his or her sleep, or the cord may be disconnected at an accident.

Figure 4:
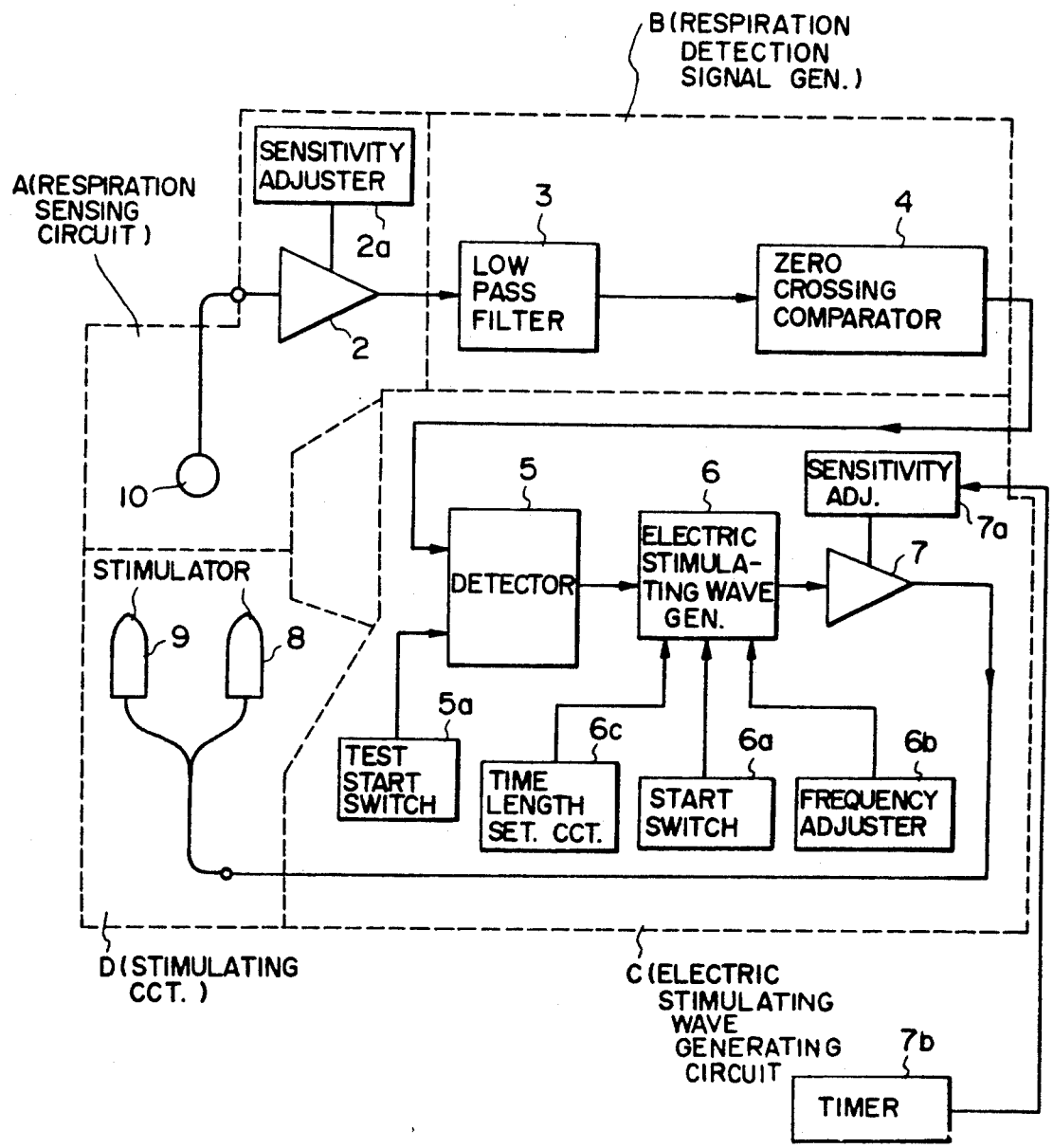
FIG. 4 is a circuit diagram illustrating another embodiment of the present invention.
Figure 6A:
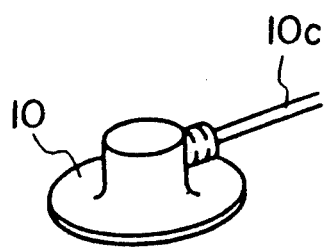
FIGS. 6A, 6B and 7 are a perspective view and sections illustrating microphone sensors employed in the present invention.
Figure 6B:
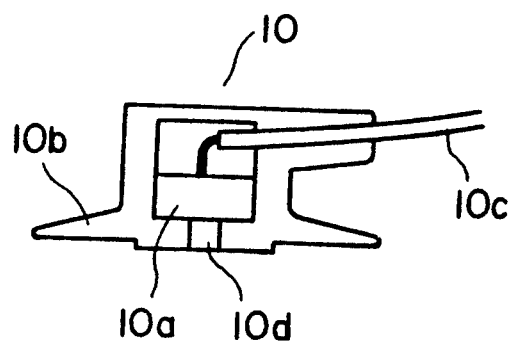

To overcome the above defect, another embodiment of the present invention is shown in FIG. 4, in which a microphone can be employed as the sensor to detect breath tones. In this case, the sensor 10 comprises a microphone 10a, a case 10b, a cord 10c and a sensing hole 10d as shown in FIGS. 6A and 6B. The microphone sensor 10 is set on the neck of a patient as shown in FIG. 5 to detect the breath tones.

Figure 7:
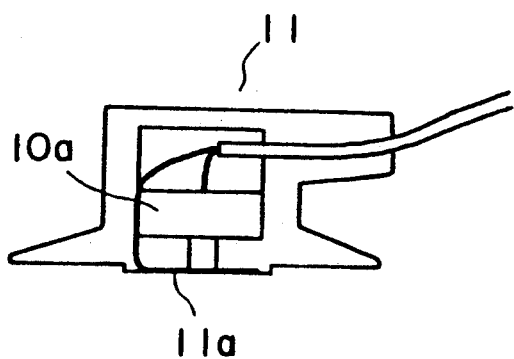
Figure 8:
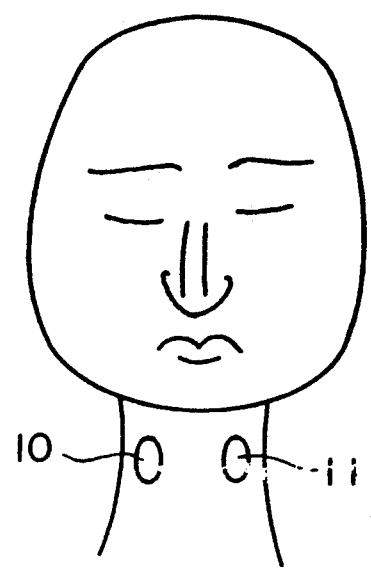

A modified sensor 11 having the microphone 10a comprises further a stimulator 11a on the surface, as shown in FIG. 7, and can be used as shown in FIG. 8 in addition to the sensor 10 at the neck.

In the embodiment shown in FIG. 4, the timer 7b is attached to the sensitivity adjuster 7a to amplify the intensity of the electric stimulating wave at a predetermined time (e.g. half an hour or one hour) from patient's bedtime, so that the lowering of stimulation on a patient by the electric stimulating wave during the patient's deep sleep is compensated for to wake up the patient. In this case, the amplification factor is 1.5 or 2 by way of example.

Since the present invention has such a construction as described above, a patient needs only to fix the sensors 1a, 1b and 1c and the stimulators 8 and 9 at predetermined positions before going to bed, in which case if a patient has a fit of apnea in patient's sleep, the electric stimulative wave generator 6 provides automatically stimulus to the genioglossus, which causes decreasing the obstruction of the upper airway and recovering the breathing. Thus, the present invention ensures the prevention of various diseases which are caused by the fit of apnea, and the invention achieved good results in clinical testing on patients.

What we claim is:

1. An apnea preventive stimulating device comprising:
    a respiration sensing circuit comprising sensors for sensing the respiration of a living patient on which the sensors are applied and developing a respiration detection signal representative of the detected respiration, said sensors comprising a sensor for sensing breathing through a left nostril, a sensor for sensing breathing through a right nostril and a sensor for sensing breathing through the mouth, said sensors being connected in parallel with one another, said respiration sensing circuit comprising means for amplifying signals from said sensors and means for varying the amplification of said signals to vary the sensitivity of said sensors;
    a respiration detection signal generator means connected with said respiration sensing circuit for receiving said respiration detection signal and producing a respiration identification signal developed only when breathing by the patient is detected by said sensors;
    an electric stimulating wave generating circuit connected with said respiration detection signal generator means for receiving said respiration identification signal, said electric stimulating wave generating circuit including a respiration identifying detector which when apnea has continued an apnea time causing any trouble after detection thereof by said respiration detection signal generator means generates electrical stimulating waves; and
    a stimulating circuit connected with said electric stimulating wave generating circuit and composed of genioglossus stimulators to which said electrical stimulating waves are applied for genioglossus stimulation of the patient.

2. An apnea preventive stimulating device according to claim 1, in which said sensors are thermistors.

3. An apnea preventive stimulating device according to claim 1, in which said electrical stimulating wave generating circuit comprises means for generating electrical stimulating waves having a frequency of 40 to 150 Hz and pulse peak values of 1 to 50 v.

4. An apnea preventive stimulating device comprising:
- a respiration sensing circuit comprising sensors for sensing the respiration of a living patient on which the sensors are applied and developing a respiration detection signal representative of the detected respiration, said sensors comprising a sensor for sensing breathing through a left nostril, a sensor for sensing breathing through a right nostril and a sensor for sensing breathing through the mouth, said sensors being connected in parallel with one another, said respiration sensing circuit comprising means for amplifying signals from said sensors and means for varying the amplification of said signals to vary the sensitivity of said sensors;
- a respiration detection signal generator means connected with said respiration sensing circuit for receiving said respiration detection signal and producing a respiration identification signal developed only when breathing by the patient is detected by said sensors;
- an electric stimulating wave generating circuit connected with said respiration detection signal generator means for receiving said respiration identification signal including a respiration identifying detector which when apnea has continued 5 to 10 seconds after detection thereof by said respiration detection signal generator means generates electrical stimulating waves having a frequency of 40 to 150 Hz and a pulse peak values of 1 to 50 V; and
- a stimulating circuit connected with said electrical stimulating wave generating circuit and composed of genioglossus stimulators to which said electrical stimulating waves are applied for genioglossus stimulation of the patient.

* * * * *